US010695156B2

(12) United States Patent
Ostrovsky et al.

(10) Patent No.: US 10,695,156 B2
(45) Date of Patent: *Jun. 30, 2020

(54) ADJUSTABLE IMPLANTS AND METHODS OF IMPLANTING THE SAME

(71) Applicant: Boston Scientific Scimed, Inc., Maple Grove, MN (US)

(72) Inventors: Isaac Ostrovsky, Wellesley, MA (US); Jozef Slanda, Milford, MA (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,944

(22) Filed: Jul. 11, 2016

(65) Prior Publication Data

US 2016/0317273 A1 Nov. 3, 2016

Related U.S. Application Data

(63) Continuation of application No. 13/190,229, filed on Jul. 25, 2011, now Pat. No. 9,402,615.

(Continued)

(51) Int. Cl.
*A61F 2/00* (2006.01)
*A61B 17/04* (2006.01)
(Continued)

(52) U.S. Cl.
CPC ........ *A61F 2/0063* (2013.01); *A61B 17/0401* (2013.01); *A61B 17/3468* (2013.01);
(Continued)

(58) Field of Classification Search
CPC .......................... A61B 2017/0446–0462; A61B 2017/045–0453
See application file for complete search history.

(56) References Cited

U.S. PATENT DOCUMENTS 6,010,447 A * 1/2000 Kardjian ............... A61F 2/0045
128/DIG. 25
8,523,902 B2 * 9/2013 Heaven ............... A61B 17/0401
606/232
(Continued)

FOREIGN PATENT DOCUMENTS

WO 2005122954 A1 12/2005
WO 2006037131 A2 4/2006
(Continued)

OTHER PUBLICATIONS

Final Response for U.S. Appl. No. 13/190,229, filed Feb. 18, 2016, 9 pages.

(Continued)

*Primary Examiner* — Catherine B Kuhlman
(74) *Attorney, Agent, or Firm* — Brake Hughes Bellermann LLP

(57) ABSTRACT

In one embodiment, an implant includes a support member configured to be placed within a body of a patient and provide support to a portion of the body of the patient, a tether coupled to an end portion of the support member; and an anchor configured to be disposed within a tissue of the body of the patient to help retain the implant in place within the body of the patient. The tether is coupled to the anchor such that the tether may move with respect to the anchor in a first direction but is retrained from moving in a second direction. In one embodiment, a method of placing an implant within a body of a patient includes making an incision in the body of the patient, inserting the implant into the body of the patient through the incision, placing the implant within the body of the patient such that a support member provides support to a portion of the body and an anchor helps retain the implant in place within the body of (Continued)

the patient, closing the incision, and adjusting the tension of the implant after closing the incision.

14 Claims, 7 Drawing Sheets

Related U.S. Application Data

(60) Provisional application No. 61/371,033, filed on Aug. 5, 2010.

(51) Int. Cl.
*A61F 2/08* (2006.01)
*A61B 17/34* (2006.01)
*A61B 17/00* (2006.01)

(52) U.S. Cl.
CPC .. *A61F 2/0045* (2013.01); *A61B 2017/00805* (2013.01); *A61B 2017/0448* (2013.01); *A61B 2017/0459* (2013.01); *A61F 2/0811* (2013.01); *A61F 2002/0072* (2013.01); *A61F 2002/0829* (2013.01)

(56) References Cited

U.S. PATENT DOCUMENTS

| | | | |
|---|---|---|---|
| 9,402,615 B2 * | 8/2016 | Ostrovsky | A61B 17/0401 |
| 2004/0254593 A1 * | 12/2004 | Fallin | A61B 17/0487 606/148 |
| 2005/0251157 A1 | 11/2005 | Saadat et al. | |
| 2006/0089525 A1 | 4/2006 | Mamo et al. | |
| 2006/0106423 A1 | 5/2006 | Weisel et al. | |
| 2006/0282081 A1 * | 12/2006 | Fanton | A61B 17/0401 606/232 |
| 2006/0293710 A1 * | 12/2006 | Foerster | A61B 17/0401 606/232 |
| 2009/0137861 A1 * | 5/2009 | Goldberg | A61B 17/0493 600/30 |
| 2009/0137862 A1 | 5/2009 | Evans et al. | |
| 2011/0112357 A1 | 5/2011 | Chapman et al. | |

FOREIGN PATENT DOCUMENTS

| | | |
|---|---|---|
| WO | 2007149348 A2 | 12/2007 |
| WO | 2009111802 A1 | 9/2009 |
| WO | 2012018636 A1 | 2/2012 |

OTHER PUBLICATIONS

U.S. Appl. No. 13/190,229, Non-Final Office Action dated Oct. 2, 2013, 14 pages.
Final Office Action for U.S. Appl. No. 13/190,229, dated Dec. 18, 2015, 12 Pages.
Non Final Office Action for U.S. Appl. No. 13/190,229, dated Apr. 23, 2014, 16 pages.
Non-Final Office Action for U.S. Appl. No. 13/190,229, dated Mar. 19, 2015, 17 pages.
Non-Final Office Action Response for U.S. Appl. No. 13/190,229, filed Dec. 23, 2013, 8 pages.
Non-Final Office Action Response for U.S. Appl. No. 13/190,229, filed Jul. 23, 2014, 7 Pages.
Notice of Allowance for U.S. Appl. No. 13/190,229, dated Mar. 30, 2016, 7 Pages.
Response to Non-Final Office Action for U.S. Appl. No. 13/190,229, filed Jun. 10, 2015, 8 pages.
First Examiner Report for AU Application No. 2011286211, dated Feb. 14, 2014, 4 Pages.
Communication Pursuant to Rules 161(1) and 162 EPC for EP Application No. 11749603.4, dated Apr. 4, 2013, 2 pages.
Response to Communication Pursuant to Rules 161(1) and 162 EPC for EP Application No. 11749603.4, filed Oct. 7, 2013, 9 pages.
International Search Report and Written Opinion for International Application No. PCT/US2011/045394, dated Feb. 14, 2013, 10 pages.

* cited by examiner

ADJUSTABLE IMPLANTS AND METHODS OF IMPLANTING THE SAME

CROSS-REFERENCE TO RELATED APPLICATIONS

This application is a Continuation of, and claims priority to, U.S. patent application Ser. No. 13/190,229, filed on Jul. 25, 2011, entitled "ADJUSTABLE IMPLANTS AND METHODS OF IMPLANTING THE SAME", which, in turn, claims priority to U.S. Patent Application No. 61/371,033, filed on Aug. 5, 2010, entitled "ADJUSTABLE IMPLANTS AND METHODS OF IMPLANTING THE SAME", the disclosures of which are incorporated by reference herein in their entirety.

TECHNICAL FIELD

This disclosure relates generally to medical devices and more particularly to implants configured to provide support within a body of a patient and methods for securing such implants with the body of the patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension of a portion of a body of a patient. For example, a hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of anchors disposed at various fixation points.

It may be difficult to apply the correct tension to existing implants during the implantation procedure. Additionally, it may be difficult to adjust the tension of existing implants at a time after the completion of the implantation procedure. Thus, it would be beneficial to provide an implant that facilitates tensioning of the implant during and at a time after the implantation procedure.

SUMMARY

In one embodiment, an implant includes a support member configured to be placed within a body of a patient and provide support to a portion of the body of the patient, a tether coupled to an end portion of the support member; and an anchor configured to be disposed within a tissue of the body of the patient to help retain the implant in place within the body of the patient. The tether is coupled to the anchor such that the tether may move with respect to the anchor in a first direction but is retrained from moving in a second direction. In one embodiment, a method of placing an implant within a body of a patient includes making an incision in the body of the patient, inserting the implant into the body of the patient through the incision, placing the implant within the body of the patient such that a support member provides support to a portion of the body and an anchor helps retain the implant in place within the body of the patient, closing the incision, and adjusting the tension of the implant after closing the incision.

DETAILED DESCRIPTION

Figure 1:
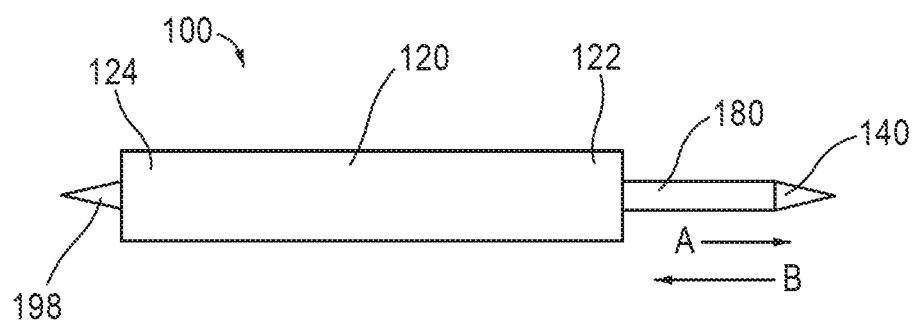
FIG. 1 is a schematic illustration of an implant according to an embodiment of the invention.

The devices and methods described herein are generally directed to implants configured to be disposed within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient. The implants and procedures described herein may be used in a female patient or a male patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

Various embodiments of implants are described herein. The implants can be delivered to various parts of the body of the patient using a variety of different method and delivery devices. The implants and methods disclosed herein include pelvic floor implants, but the implants may be configured to be placed and methods may be used to place such implants in any portion of the body of the patient.

An implant can be delivered to a pelvic region of a patient using a variety of different delivery devices, only some examples of which are described herein.

FIG. 1 is a schematic illustration of an implant 100 according to an embodiment. The implant 100 includes a support member 120, a mesh carrier or anchor 140, and a tether 180. The implant 100 is configured to be placed within a body of a patient to provide support to a portion of the body of the patient. For example, in some embodiments, the support member 120 of the implant 100 is configured to be placed proximate or adjacent a bladder of a patient to provide support to the bladder of the patient. In other embodiments, the support member 120 of the implant is configured to support the urethera or bladder neck of a patient. In yet other embodiments, the support member 120 of the implant 100 is configured to be placed adjacent another portion of the body to provide support to another portion of the body.

The support member includes end portions 122 and 124. The tether 180 is coupled to end portion 122 of the support member 120 and is coupled to the anchor 140 such that the tether 180 is configured to move with respect to the anchor 140 in a first direction and is restrained from moving with respect to the anchor in a second direction. In some embodiments, the second direction is opposite the first direction. In other embodiments, the second direction is substantially opposite the first direction. In yet other embodiments, the second direction is different than the first direction. In the illustrated embodiment, the tether 180 is coupled to the anchor 140 such that the tether 180 may move with respect to the anchor 140 in direction A and is restrained from moving with respect to the anchor 140 in direction B.

In some embodiments, the tether 180 is a suture or thread. In other embodiments, the tether 180 is a narrow portion of mesh material. In further embodiments, the tether 180 is another type of material.

Any known method of coupling the tether 180 to the end portion 122 of the support member 120 may be used. For example, the tether 180 may be tied to support member. In other embodiments, an adhesive is used to couple the tether 180 to the support member.

In some embodiments, rather than a tether extending between the support member 120 and the anchor 140, the support member 120 is directly coupled to the anchor 140. For example, the support member 120 may include a narrow flexible portion that extends from a body portion of the support member to the anchor 140.

The implant 100 also includes a mesh carrier or anchor 198 coupled to end portion 124 of the support member 120. In some embodiments, the anchor 198 is directly coupled to the end portion 124 of the support member 120. In other embodiments, a tether is coupled between the end portion 124 and the anchor 198. Any known mechanism may be used to couple the anchor 190 to the support member 120. For example, an adhesive may be used to couple the anchor 198 to the support member 120. Alternatively, the anchor 198 may surround and be frictionally coupled to the support member 120.

The anchors 140 and 198 are configured to be disposed in bodily tissue and provide a support for implant 100. Specifically, once disposed within bodily tissue, the anchors 140 and 198 are configured to help retain the implant 100 in place within a body of a patient. In some embodiments, the anchors 140 and 198 are configured to be disposed within pelvic tissue of a patient. In other embodiments, the anchors 140 and 198 are configured to be disposed in other bodily tissue, such as muscle tissue.

In some embodiments, the anchors 140 and 198 include barbs or projections that are configured to help secure the anchors 140 and 198 in place within the bodily tissue. In some embodiments, the anchors 140 and 198 do not include any sort of structure for securing the anchors in place within the body of the patient.

Any known method of placing implants within a body of a patient may be used to place implant 100 within a body of a patient. For example, in embodiments where the implant 100 is being placed in a pelvic region of a female patient, a vaginal incision may be made and the implant 100 may be placed into the body of the patient through the vaginal incision. In some embodiments, an insertion tool that is configured to engage and place the anchors 140 and 198 at an appropriate location within the body of the patient. In some embodiments, a Solyx™ delivery needle as sold by Boston Scientific Corporation may be used to deliver the anchors 140 and 198 into the appropriate locations within the body of the patient. In other embodiments, the implant 100 is inserted into the body of the patient through a different bodily incision and the anchors 140 and 198 are placed using a different type of insertion tool.

As the tether 180 is configured to move with respect to the anchor 140 in the direction A the effective length of the implant 100 may be decreased. Specifically, the length of the implant 100 (or the length of the implant between the anchors 140 and 198) may be decreased by moving the tether 180 in direction A with respect to the anchor 140. Thus, the implant 100 may be placed within a body of a patient and the tension of the implant may be adjusted by moving the tether 180 in direction A with respect to the anchor 140.

In some embodiments, the tether 180 includes an end portion that, after the implant 100 is placed within a body of a patient, may be disposed outside of the body of the patient. In some embodiments, applying a force, such as by pulling, on the end portion of the tether 180 from a location outside of the body will move the tether 180 in direction A with respect to the anchor 140. Thus, the effective length of the implant 100 may be decreased at a time after the implantation procedure. In other words, because the locations of the anchors 140 and 198 remain in place within the body of the patient when the tether 180 is moved in direction A with respect to the anchor 140, the tension of the implant 100 may be adjusted after the procedure to place the implant within the body of the patient has been completed. For example, in some embodiments, the tension of the implant 100 may be adjusted 24 hours after the procedure to place the implant 100 within the body of the patient has been completed. In other embodiments, the tension of the implant 100 may be adjusted 48 hours or more after the procedure to place the implant 100 within the body of the patient has been completed.

In some embodiments, the end portion of the tether 180 is disposed inside of the body of the patient proximate an incision that was made during the implantation procedure. In such embodiments, a physician may easily access the end portion of the tether 180 at a time after the implantation procedure to adjust the tension of the implant 100.

The implant 100 may be formed of any biocompatible material. In some embodiments, the support member 120 is formed of a mesh material. For example, the support member 120 may be formed of Advantage® mesh or the Polyform™ synthetic mesh, both as sold by Boston Scientific Corporation. In some embodiments, in the support member 120 may be formed of a polymer material. In some embodiments, the material of the support member 120 allows for tissue in-growth to secure the implant 100 to the bodily tissue of the patient.

In some embodiments, the support member 120 includes tangs to help retain the implant in place within the body of the patient. In such embodiments, the tang or tangs are configured to engage the bodily tissue surrounding the support member 120 help retain the implant 100 in place within the body of the patient. The terms "tanged" or "tangs" as used herein mean roughened or jagged edges or areas, such as can result from cutting a woven or knit mesh material.

While the implant 100 is illustrated and described as including anchors 140 and 198, in some embodiments, the implant 100 does not include anchors. In such embodiments, the effective length of the implant may be modified or adjusted without reference to the anchors. For example, end portions of the implant may be coupled to different portions of the body of the patient. The length of the implant may then be adjusted.

Figure 2:
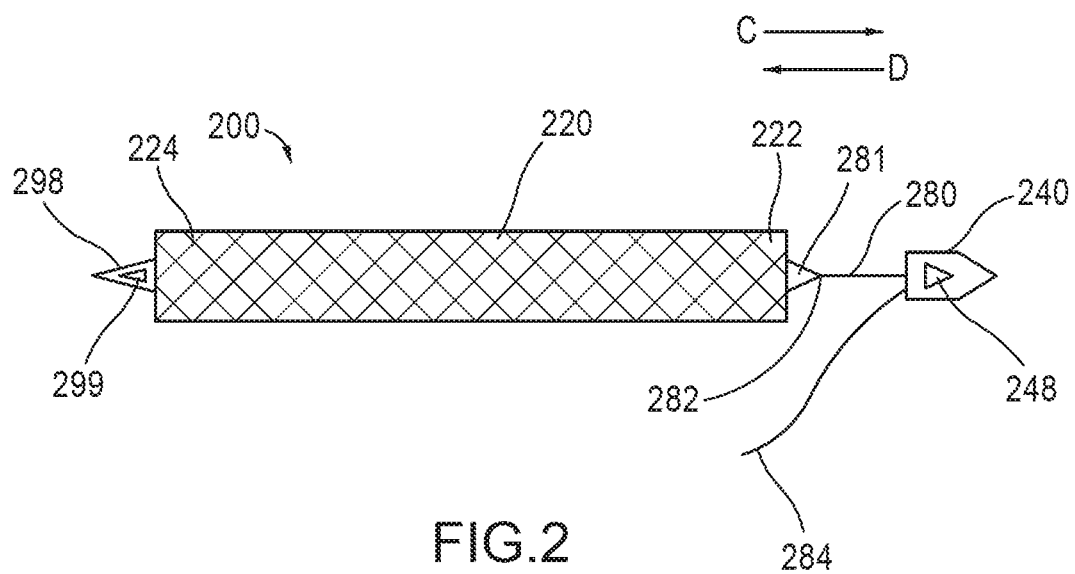
FIG. 2 is a top view of an implant according to an embodiment of the invention.
Figure 3:
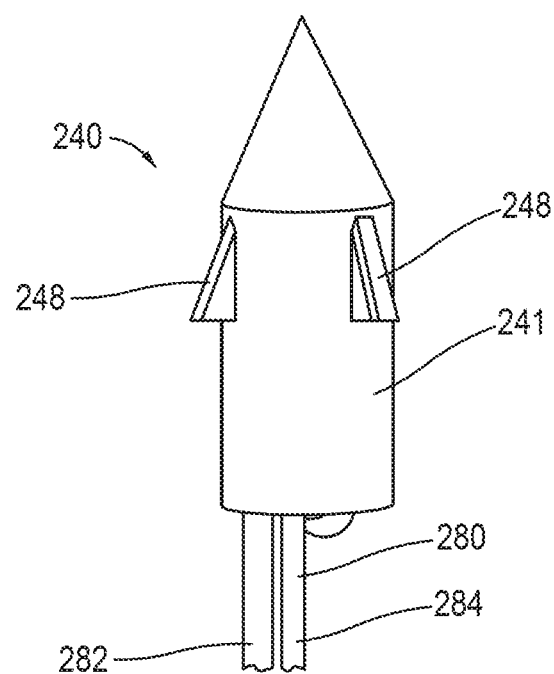
FIG. 3 is a side view of an anchor of the implant of FIG. 2.
Figure 4:
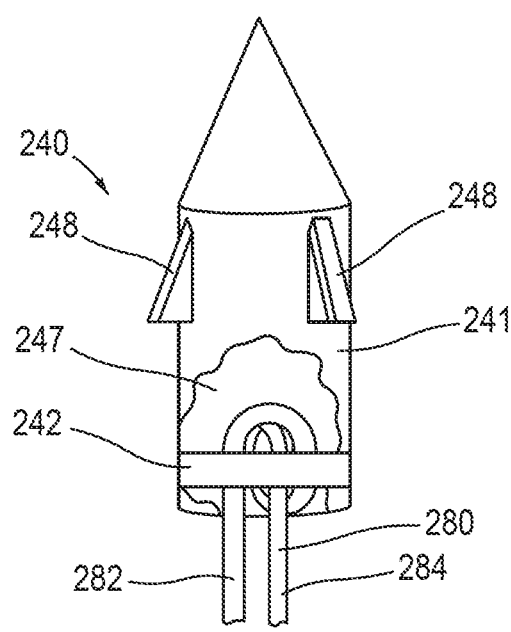
FIG. 4 is a break-away view of the anchor of FIG. 3.

FIG. 2 is a top view of an implant 200 according to an embodiment. The implant 200 includes a support member 220, anchors 240 and 298, and a tether 280. The implant 200 is configured to be placed within a body of a patient to provide support to a portion of the body of the patient. For example, in some embodiments, the support member 220 of the implant 200 is configured to be placed proximate or adjacent a bladder of a patient to provide support to the bladder of the patient. In other embodiments, the support member 220 of the implant 200 is configured to be placed adjacent another portion of the body to provide support to another portion of the body.

The support member includes end portions 222 and 224. The tether 280 includes end portions 282 and 284. End portion 282 of the tether 280 is coupled to end portion 222 of the support member 220. The tether 280 is coupled to the anchor 240 such that the tether 280 is configured to move with respect to the anchor 240 in a first direction and is restrained from moving with respect to the anchor 240 in a second direction. In the illustrated embodiment, the tether 280 is coupled to the anchor 240 such that the tether 280 may move with respect to the anchor 240 in direction C and is restrained from moving with respect to the anchor 240 in direction D. Specifically, end portion 282 may move with respect to the anchor 240 in direction C and is restrained from moving with respect to the anchor 240 in direction D.

Any known method of coupling the tether 280 to the end portion 222 of the support member 220 may be used. For example, the tether 280 may be tied to support member 220. In other embodiments, an adhesive is used to couple the tether 280 to the support member 220. In the illustrated embodiment, a coupler 281 is coupled between the support member 220 and the tether 280.

As best illustrated in FIGS. 3-6, the anchor 240 includes a lock member 242. In the illustrated embodiment, the lock member 242 is disposed within a cavity 247 defined by a body 241 of the anchor 240. In some embodiments, the lock member 242 is formed separately from the body 241 of the anchor 240 and is coupled to the body 241 of the anchor. Any known coupling methods may be used to couple the lock member 242 to the body 241 of the anchor 240. For example, an adhesive may be used to couple the lock member 242 to the body 241 of the anchor 240. In other embodiments, the lock member 242 and the body 241 of the anchor 240 are unitarily or monolithically formed. In some embodiments, the anchor 240 is formed of a biocompatible polymer.

The lock member 242 defines lumens 243, 244, 245, and 246. The lumens 243, 244, 245, and 246 are configured to slideably receive the tether 280. Accordingly, the tether 280 is configured to extend through and slide within the lumens 243, 244, 245, and 246. In the illustrated embodiment, the lumens 243, 244, 245, and 246 extend in substantially parallel directions. In other embodiments, the lumens extend in directions that are not parallel to each other.

Figure 5:
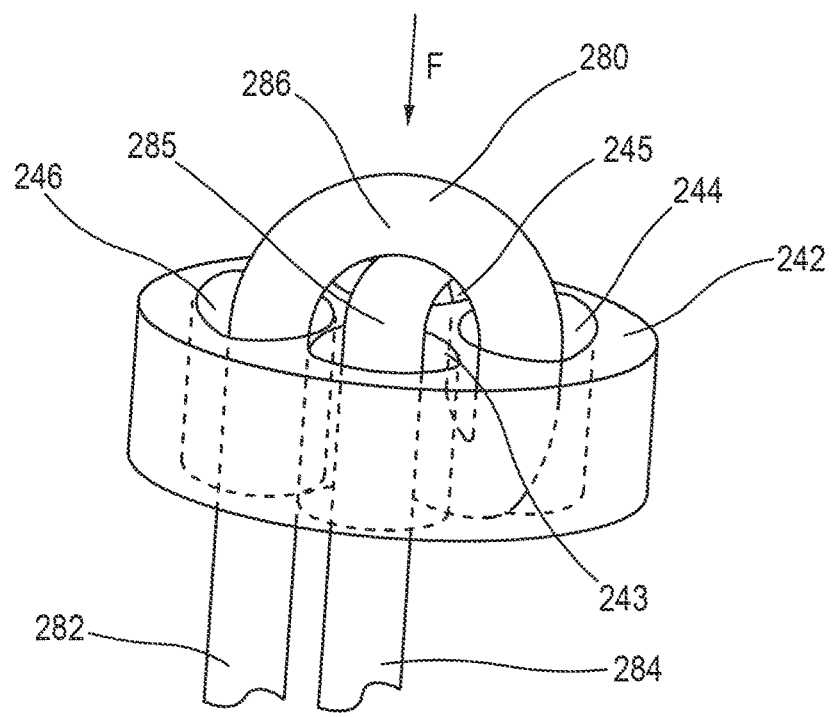
FIG. 5 is a perspective view of a portion of the anchor of the implant of FIG. 3.
Figure 6:
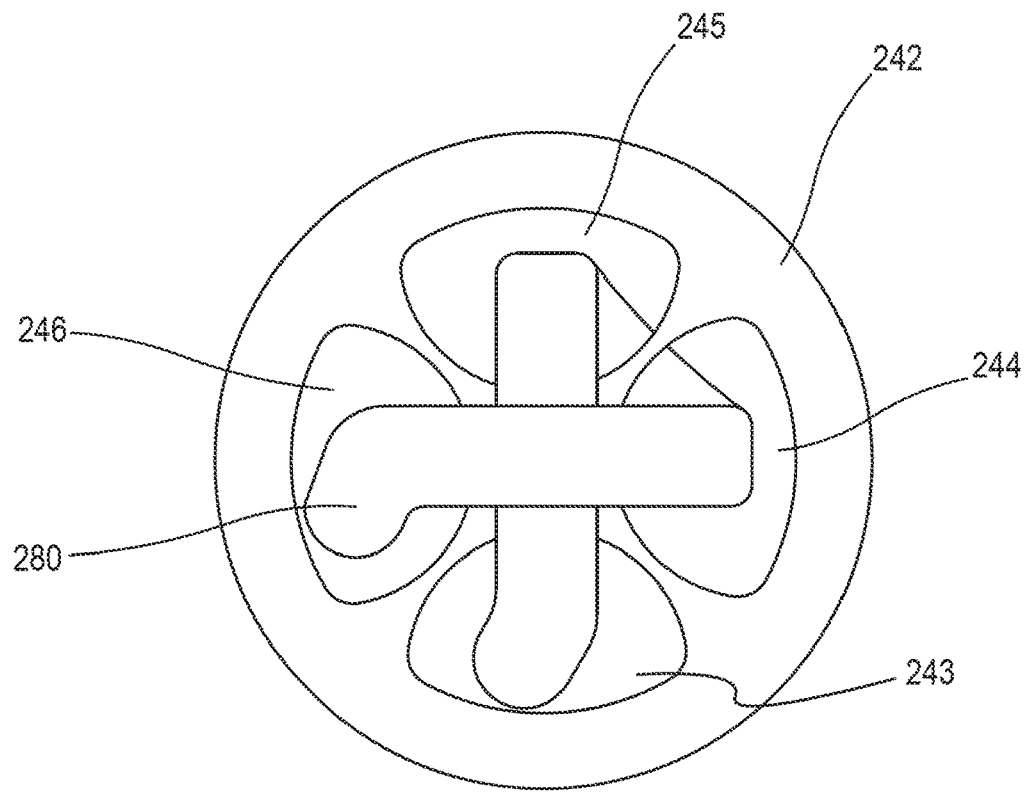
FIG. 6 is a top view of a portion of the anchor of the implant of FIG. 3.

As best illustrated in FIGS. 5 and 6, the tether 280 is threaded or extends through lumen 243 in a first direction, through lumen 244 in a second direction, through lumen 245 in the first direction, and through lumen 246 in the second direction. The tether 280 slideably passes through each of the lumens 243, 244, 245, and 246 in response to a force being applied to end portion 284 of the tether 280 (such as pulling end portion 284 in a direction away from the anchor 240 or lock member 242). Thus, as the end portion 284 of the tether 280 is pulled in a direction away from the anchor 240, the tether 280 moves in direction C with respect to the anchor 240 to shorten the effective length of the implant 200. In other words, the distance or length of the implant 200 between the anchors 240 and 298 is shortened when end portion 284 of the tether 280 is pulled in a direction away from the anchor 240.

One portion 285 of the tether 280 is disposed between another portion 286 of the tether 280 and the lock member 242. Portion 286 of the tether 280 is configured to apply a pressure or force F against portion 285 of the tether 280 when the end portion 282 of tether 280 is pulled in a direction away from the anchor 240. The pressure or force F pinches or forces the portion 285 of the tether 280 against the lock member 242 to frictionally couple the tether 280 to the lock member 242. Thus, when a force is applied to the end portion 282 of tether 280 in a direction away from the anchor 240 (or the lock member 242), the tether 280 is restrained from moving with respect to the anchor 240.

The implant 200 also includes an anchor 298 coupled to end portion 224 of the support member 220. In the illustrated embodiment, the anchor 298 is directly coupled to the end portion 224 of the support member 220. Any known mechanism may be used to couple the anchor 298 to the support member 220. For example, an adhesive may be used to couple the anchor 298 to the support member 220. In further embodiments, the anchor 298 is similar to anchor 240 and is coupled to the support member 220 in a similar manner.

The anchors 240 and 298 are configured to be disposed in bodily tissue and provide a support for implant 200. Specifically, once disposed within bodily tissue the anchors 240 and 298 are configured to help retain the implant 200 in place within a body of a patient. In some embodiments, the anchors 240 and 298 are configured to be disposed within pelvic tissue of a patient. In other embodiments, the anchors 240 and 298 are configured to be disposed in other bodily tissue, such as muscle tissue.

In the illustrated embodiment, the anchors 240 and 298 include barbs or projections 248 and 299, respectively, that are configured to help secure the anchors 240 and 298 in place within the bodily tissue.

Any known method of placing implants within a body of a female patient may be used to place implant 200 within a body of a patient. For example, in embodiments where the implant 200 is being placed in a pelvic region of a patient, a vaginal incision may be made and the implant 200 may be placed into the body of the patient through the vaginal incision. In some embodiments, the anchors 240 and 298 are each configured to be engaged by an insertion tool to be placed and delivered to a location within the body of the patient.

Figure 7A:
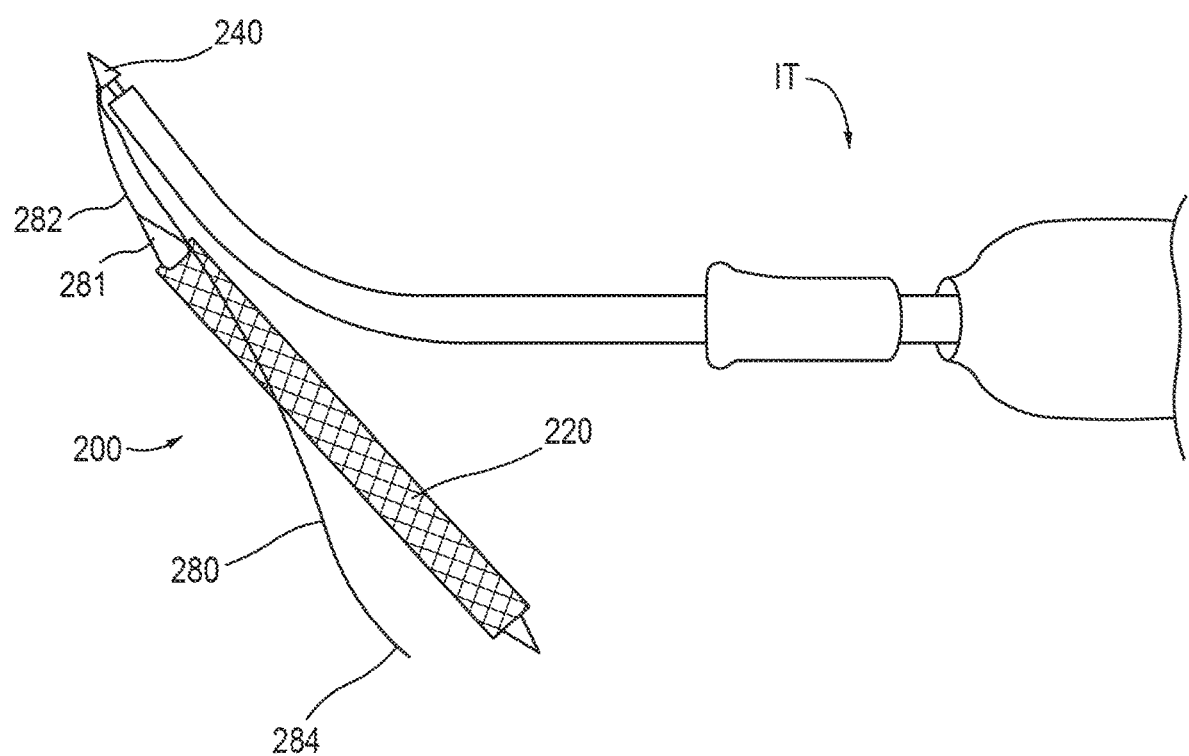
FIG. 7A is a top view of the implant of FIG. 2 coupled to an insertion tool.

For example, as illustrated in FIG. 7A, with respect to anchor 240, the anchor 240 is configured be coupled to an end portion of the insertion tool. For example, as illustrated, the anchor 240 may be configured to receive a portion of the insertion tool IT to couple the anchor 240 to the insertion tool IT. The physician may then manipulate the insertion tool IT to dispose the anchor 240 at the correct location within the body of the patient. The insertion tool IT may then be released from the anchor 240 and removed from the body of the patent to leave the anchor 240 in place within the body of the patient. In some embodiments, the insertion tool IT may include a decoupling mechanism. In other embodiments, the insertion tool IT may be released from the anchor 240 by moving the insertion tool IT in a direction away from the anchor 240. The same procedure may be used to place anchor 298 within the body of the patient.

In some embodiments, an insertion tool, such as Solyx™ as sold by Boston Scientific Corporation may be used to deliver the anchors 240 and 298 into the appropriate locations within the body of the patient. In other embodiments, the implant 200 is inserted into the body of the patient through a different bodily incision and the anchors are placed using a different type of insertion tool.

As the tether 280 is configured to move with respect to the anchor 240 in the direction C the effective length of the implant 200 may be decreased. Specifically, the length of the implant 200 (or the distance or length of the implant 200 between the anchors 240 and 298) may be decreased by moving the end portion 282 of the tether 280 in direction C with respect to the anchor 240. Thus, the implant 200 may be placed within a body of a patient and the tension of the implant may be adjusted by moving the end portion 282 of the tether 280 in direction C with respect to the anchor 240.

Figure 7B:
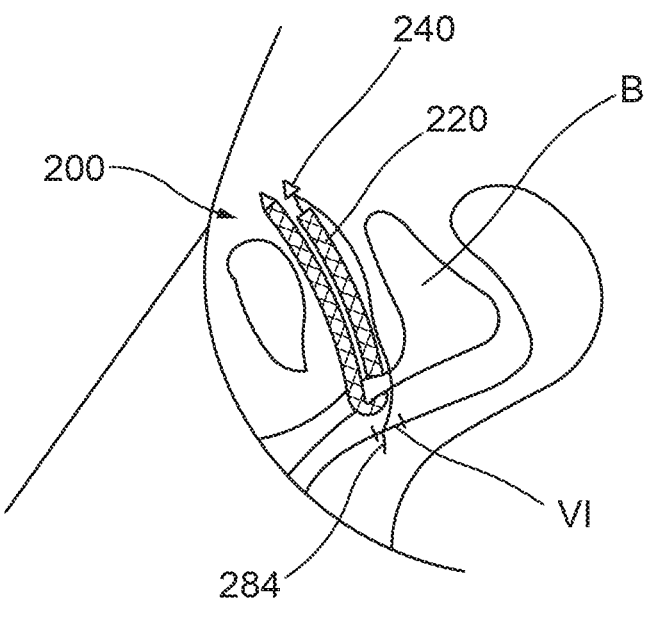
FIG. 7B is a schematic view of an implant disposed within a body of a patient.

FIG. 7B illustrates the implant 200 disposed within a pelvic region of a female patient. The support member 220 is disposed adjacent a portion of a bladder B of the patient and the anchors 240 and 298 are disposed in pelvic tissue. As illustrated, end portion 284 of the tether 280 is disposed outside of the vaginal incision VI, which was made to insert the implant 200 into the body of the patient. In other words, the end portion 284 of the tether 280 extends from a location within the body of the patient through the vaginal incision VI. In some embodiments, the end portion 284 is disposed outside of the body of the patient. In some embodiments, the end portion 284 extends through the vaginal incision VI and is disposed within the vagina V of the patient. In other embodiments, the end portion 284 does not extend from the bodily incision, but is disposed within the body of the patient at a location proximate and adjacent the bodily incision. Accordingly, in some embodiments in which the end portion 284 is disposed within the body of the patient at a location proximate and adjacent the bodily incision, a physician may easily locate the end portion 284 after the procedure to place the implant 200 within the body of the patient.

Applying a force, such as by pulling, on the end portion 284 of the tether 280 from a location outside of the body will move the tether 280 through the lock member 242 of the anchor 240 in direction C with respect to the anchor 240 (i.e., the end portion 282 of the tether 280 moves in direction C with respect to the anchor 240). Thus, the effective length of the implant 200 may be decreased at a time after the implantation procedure. In other words, the tension of the implant 200 may be adjusted after the procedure to place the implant within the body of the patient has been completed. For example, in some embodiments, the tension of the implant 200 may be adjusted 24 hours after the procedure to place the implant 200 within the body of the patient has been completed. In other embodiments, the tension of the implant 200 may be adjusted 48 hours or more after the procedure to place the implant 200 within the body of the patient has been completed.

While the described and illustrated implants include anchors, in some embodiments, the implants do not include anchors. In such embodiments, the effective length of the implant may be modified or adjusted without reference to the anchors. For example, end portions of an implant may be coupled to different portions of the body of the patient. The length of the implant may then be adjusted via a tether.

Figure 8:
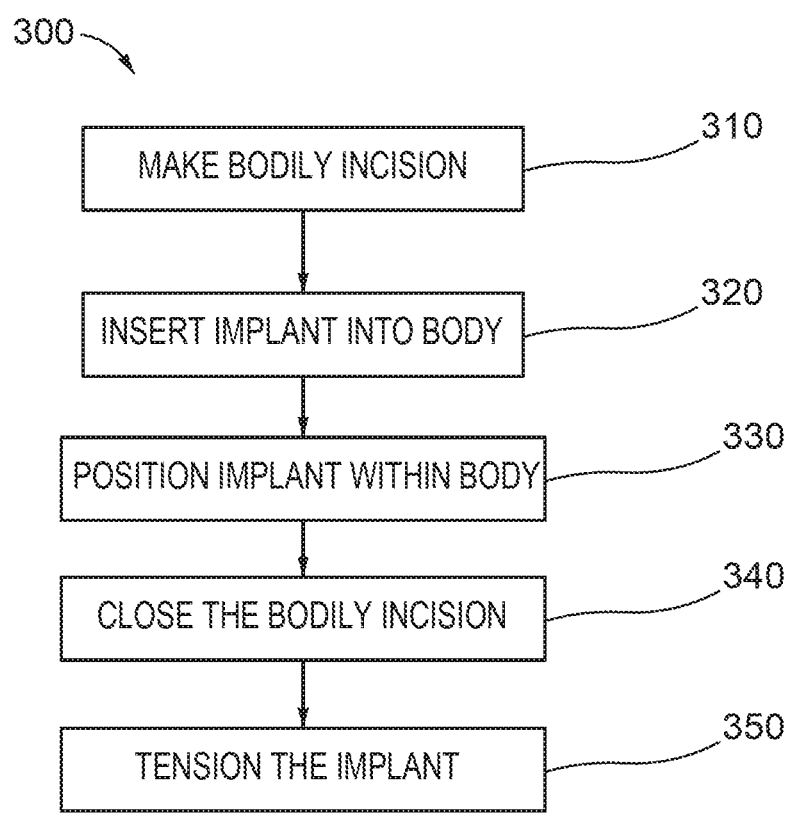
FIG. 8 is a flow chart of a procedure for placing and tensioning an implant according to an embodiment of the invention.
Figure 9:
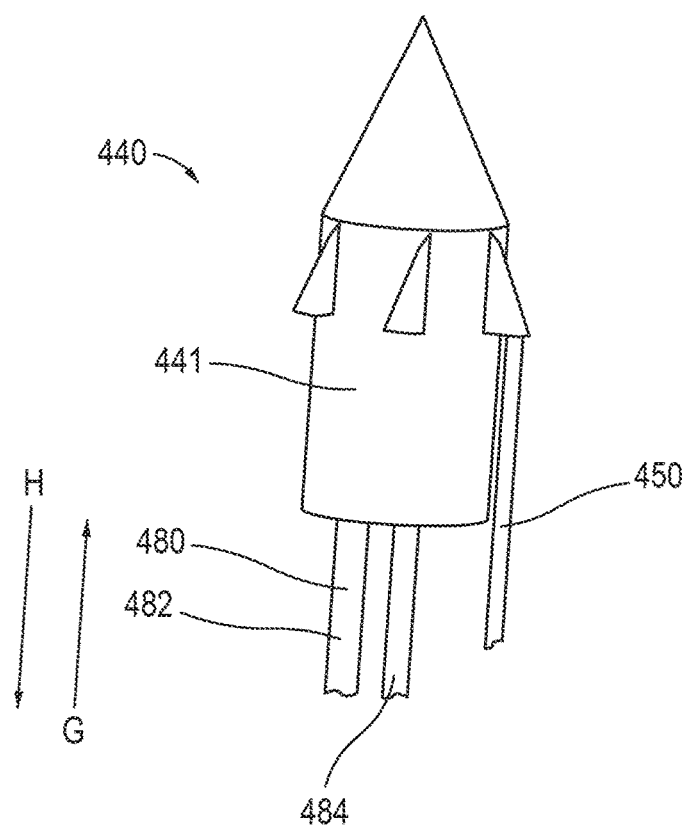
FIG. 9 is a side view of an anchor according to another embodiment of the invention.
Figure 10:
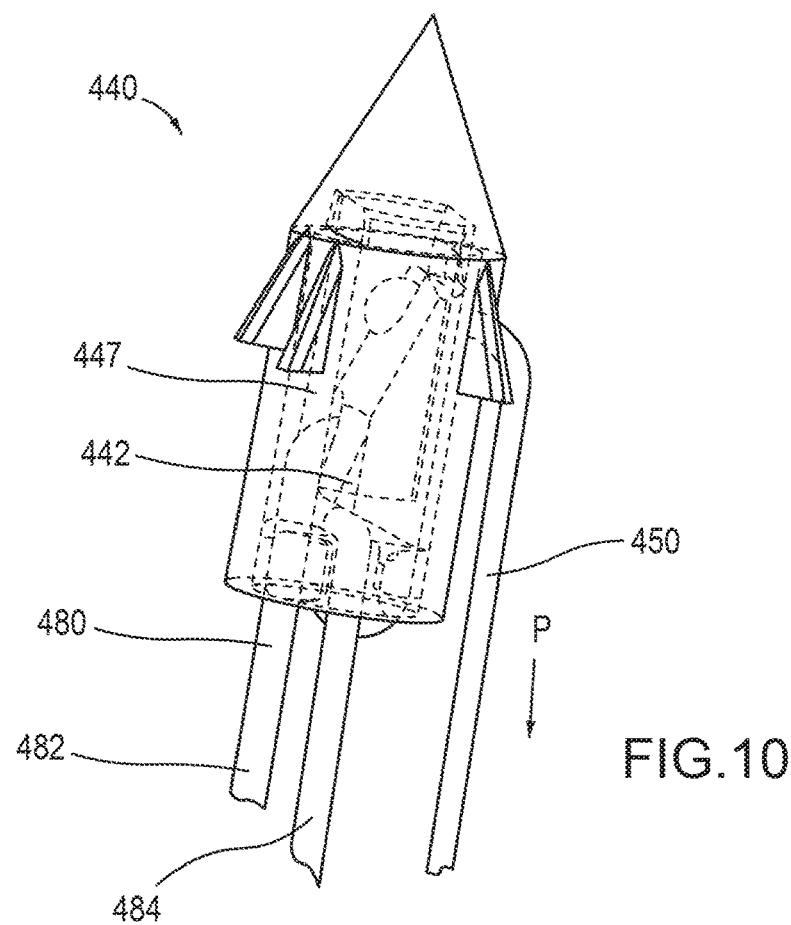
FIG. 10 is a see-through side view of the anchor of FIG. 9.

FIG. 8, is a flow chart of a method 300 that may be used to place the implant 200 within a body of a patient. The method includes at step 310 making a bodily incision in the body of the patient. In some embodiments, the bodily incision is a vaginal incision, such as an anterior vaginal incision. In other embodiments, the bodily incision is an incision other than a vaginal incision.

Step 320 includes inserting an implant into the body of the patient through the bodily incision. Then, at step 330, the implant is positioned within the body of the patient. In some embodiments, the positioning includes placing anchors of the implant into bodily tissue, such as pelvic tissue, and disposing the support member adjacent a portion of the body to be supported by the implant. In some embodiments, the support member of the implant is disposed adjacent a bladder of a patient. In other embodiments, the support member is disposed adjacent and provides support to another portion of the body of the patient, such as the uterus, or the rectum of the patient. In some embodiments, the positioning includes disposing an end portion of the tether of the implant outside of the body of the patient. In other embodiments, the positioning includes disposing an end portion of the tether at a location within the body proximate the bodily incision.

Step 340 includes suturing the bodily incision to close the bodily incision. Step 350 includes tensioning the implant after the suturing of the bodily incision. In some embodiments, the tensioning occurs hours or days after the suturing of the bodily incision. In some embodiments, the tensioning the implant includes tensioning the implant from a location outside of the body of the patient. In some embodiments, the tensioning includes applying a force to a portion of the the tether of the implant that extends from the body of the patient (or extends through the bodily incision).

FIGS. 9-12 illustrate an anchor 440 in accordance with an embodiment. The anchor 440 includes a lock member 442. In the illustrated embodiment, the lock member 442 is disposed within a cavity 447 defined by a body 441 of the anchor 440. The lock member 442 is coupled to a tether 480 which is coupled to a support member (not illustrated). For example, the support member in some embodiments is coupled to end portion 482 of the tether 480.

The lock member 442 is configured to allow the tether 480 to move in more than one direction with respect to the anchor 440. Specifically, in the illustrated embodiment, the lock member 442 is configured to allow the tether 480 to move in direction G with respect to the anchor 440 and direction H with respect to the anchor 440. As the lock member 442 of the anchor 440 allows the tether 480 to move with respect to the anchor 440, the support member may be tensioned or adjusted with respect to the anchor 440 after the implant has been placed within the body of the patient. In the illustrated embodiment, direction G is substantially opposite direction H. In other embodiments, the directions are not opposite each other.

Figure 11:
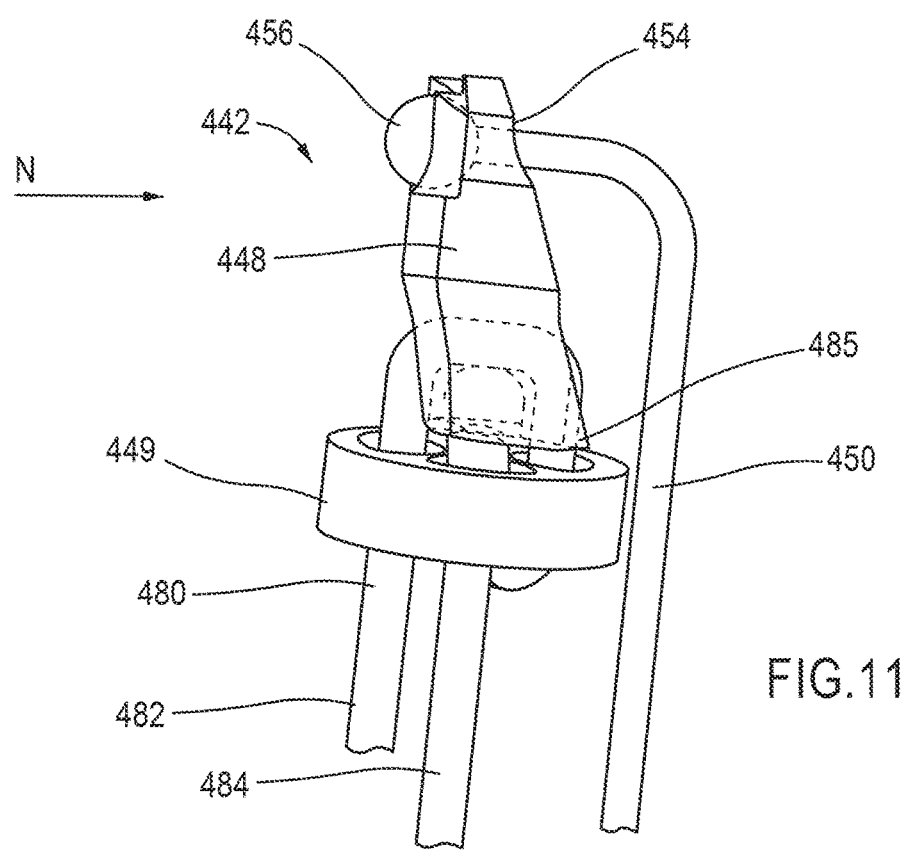
FIG. 11 is a side view of a portion of the anchor of FIG. 9 in a first configuration.
Figure 12:
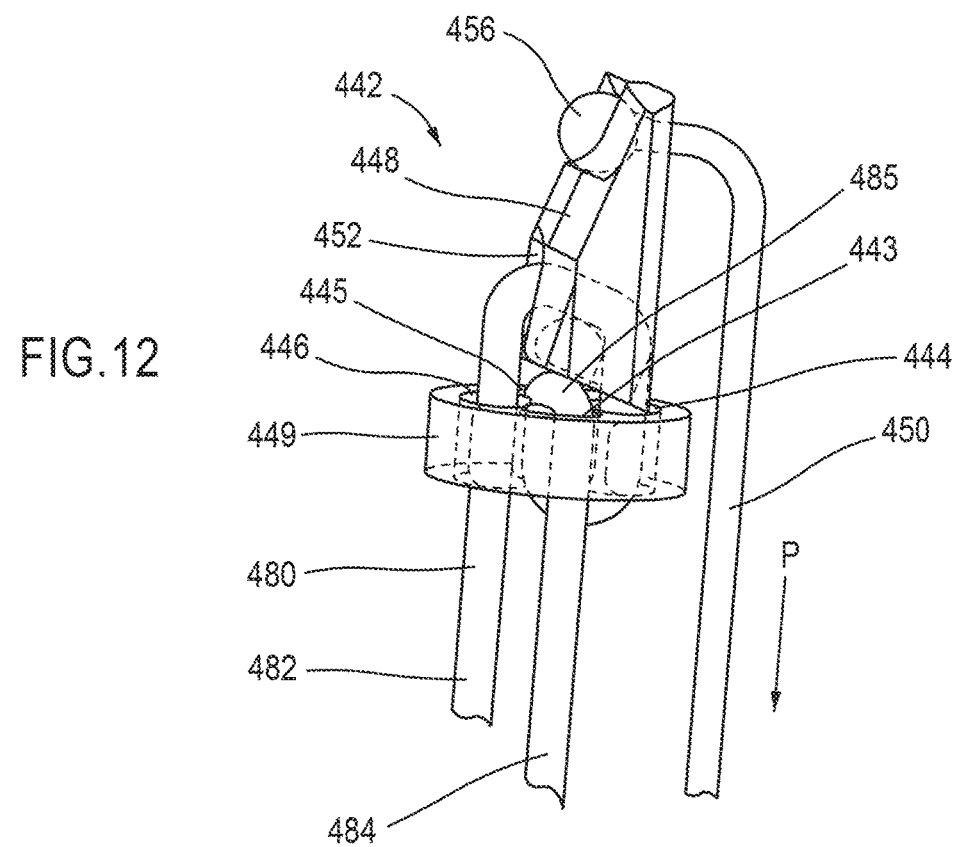
FIG. 12 is a side view of a portion of the anchor of FIG. 9 in a second configuration.

As best illustrated in FIGS. 11 and 12, the lock member 442 includes a first portion 448 and a second portion 449. The first portion 448 is movably coupled to the second portion 449. The second portion 449 of the lock member 442 is fixedly coupled to the body 441 of the anchor 440.

In the illustrated embodiment, the first portion 448 is pivotally coupled to the second portion 449. Any known method may be used to couple the first portion 448 of the lock member 442 to the second portion 449 of the lock member 442. For example, a hinge may be coupled to each of the first portion 448 and the second portion 449 to pivotally couple the first portion 448 to the second portion 449. In other embodiments, a flexible member may be disposed between the first portion 448 and the second portion 449 to pivotally couple the first portion 448 to the second portion 449.

The lock member 442 may be placed in a first configuration (as illustrated in FIG. 11) and a second configuration (as illustrated in FIG. 12). Specifically, the first portion 448 of the lock member 442 is pivoted in the direction of arrow N with respect to the second portion 449 of the lock member 442 to convert the lock member 442 from the first configuration to the second configuration.

In the illustrated embodiment, the lock member 442 includes an activation member 450. The activation member 450 is coupled to the first portion 449 of the lock member 442 and is configured to convert or move the lock member 442 from its first configuration to its second configuration. Specifically, the activation member 450 is coupled to the first portion 448 such that pulling on the activation member 450 in the direction of arrow P will cause the first portion 448 to move in the direction of arrow N with respect to the second portion 449 to convert the lock member from its first configuration to its second configuration.

Any known method may be used to couple the activation member 450 to the first portion 448 of the lock member 442. In the illustrated embodiment, the first portion 448 of the lock member 442 defines a lumen 454. The activation member 450 extends through the lumen 454 and includes an enlarged portion 456 that is configured to retain the activation member 450 coupled to the first portion 448 of the lock member 442. In other embodiments, an adhesive is used to couple the activation member 450 to the first portion 448.

In some embodiments, the lock member 442 is biased to its first configuration (as illustrated in FIG. 11). In other embodiments, the lock member 442 is biased to its second configuration (as illustrated in FIG. 12). In some embodiments, the lock member 442 is not biased to either of its configuration.

The second portion 449 of the lock member 242 defines lumens 443, 444, 445, and 446. The lumens 443, 444, 445, and 446 are configured to slideably receive the tether 480. Accordingly, the tether 480 is configured to extend through and slide within the lumens 443, 444, 445, and 446. In the illustrated embodiment, the lumens 443, 444, 445, and 446 extend in substantially parallel directions. In other embodiments, the lumens extend in directions that are not parallel to each other.

The first portion 448 of the lock member 442 defines a lumen 452. The tether 480 passes through and is slideabley coupled within lumen 452 of the first portion 448 and lumens 443, 444, 445, and 446 of the second portion 449. Specifically, in the illustrated embodiment, a portion of the tether 480 that passes through lumen 452 of the first portion 448 is located between the portion of the tether 480 that passes through lumen 444 of the second portion 449 and the portion of the tether 480 that passes through lumen 446 of the second portion 449.

When the lock member is in its first configuration or its second configuration, the tether 480 slideably passes through each of the lumens 452, 443, 444, 445, and 446 in response to a force being applied to end portion 484 of the tether 480 (such as pulling end portion 284 in a direction away from the anchor 440). Thus, as the end portion 484 of the tether 480 is pulled in a direction away from the anchor 440, the tether 480 moves in a direction with respect to the anchor 440 to shorten the effective length of the implant. Thus, additional tension may be applied to the implant and/or support member after the implant has been placed within the body of the patient.

As best illustrated in FIGS. 11 and 12, one portion 485 of the tether 480 is disposed between the first portion 448 of the lock member 442 and the second portion 449 of the lock member 442. The first portion 448 of the lock member 440 is configured to apply a pressure or force against portion 485 of the tether 480 when the lock member is in its first configuration (as illustrated in FIG. 11) and the end portion 282 of tether 480 is pulled in a direction away from the anchor 440. For example, in one embodiment, the tether applies a force to the first portion 488 of the lock member 442 to pivot the first portion 448 towards the portion 485 of the tether 480. The pressure or force pinches or forces the portion 485 of the tether 480 between the first portion 448 and the second portion 449 of the lock member 442 to frictionally couple the tether 480 to the lock member 442. Thus, tether 480 is restrained from moving with respect to the anchor 440.

When the lock member 442 is in its second configuration (as illustrated in FIG. 12), the first portion 448 is pivoted away from the portion 445 of the tether 480 disposed between the first portion 448 and the second portion 449, the tether 480 is free to move with respect to the lock member 442 in either direction. Accordingly, a force may be applied to the activation member 450 in the direction of arrow P to convert the lock member 442 to its second configuration. End portion 482 of the tether 480 may then be moved away from the anchor 440. Thus, the effective length of the implant can be increased. In other words, the length of the implant or support portion between the anchors may be increased. In one embodiment, once the implant is placed within the body, the end portion 482 of the tether 480 may be moved away from the anchor 440 by applying a pressure to the organ that is being supported by the implant. For example, when the support member of the implant is placed adjacent a urethera of a patient, a downward force may be applied on the urethera (i.e., by a physician) to move the end portion 482 away from the anchor 480 and lengthen the implant.

In one embodiment, the tether 480 and the activation member 450 are marked such that the physician may distinguish the two items. For example, in some embodiments, the tether 280 if of one color and the activation member 450 is of another color. In other embodiments, other markings are disposed on the tether 480 and activation member 450.

Any number of methods may be used to place an implant that includes anchor 440 within a body of a patient. For example, in one embodiment, the method includes making a bodily incision in the body of the patient, inserting an implant into the body of the patient through the bodily incision, and positioning the implant within the body of the patient. In some embodiments, the positioning includes placing anchors of the implant into bodily tissue, such as pelvic tissue, and disposing the support member adjacent a portion of the body to be supported by the implant. In some embodiments, the support member of the implant is disposed adjacent a bladder of a patient. In other embodiments, the support member is disposed adjacent and provides support to another portion of the body of the patient, such as the uterus, or the rectum of the patient. In some embodiments, the positioning includes disposing end portion 484 of the tether 480 and an end portion of the activation member 450 outside of the body of the patient. In other embodiments, the positioning includes disposing end portion 484 of the tether 480 and an end portion of the activation member 450 at a location within the body proximate the bodily incision. The bodily incision may then be closed.

Once the bodily incision is closed, the tension or length of the implant may be adjusted. In some embodiments, the tensioning occurs hours or days after the suturing of the bodily incision. In some embodiments, the tensioning the implant includes tensioning the implant from a location outside of the body of the patient.

In some embodiments, the additional tension may be applied to the implant (i.e., the effective length of the implant is shortened) by applying a force or pulling the end portion 484 of the tether 480 that extends from the body of the patient.

In some embodiments, the tension of the implant may be loosened (i.e., the effective length of the implant is increased) by applying a force or pulling and end portion of the activation member 450 that extends from the body of the patient (to place the lock member 442 in its second configuration) and applying a downward force on the portion of the body that is being supported by the implant. For example, if the implant is supporting the urethera, a downward pressure or force may be applied to the urethera to loosen the tension of the implant.

In one embodiment, an implant includes a support member configured to be placed within a body of a patient and provide support to a portion of the body of the patient, a tether coupled to an end portion of the support member, and an anchor configured to be disposed within a tissue of the body of the patient to help retain the implant in place within the body of the patient. The tether is coupled to the anchor such that the tether may move with respect to the anchor in a first direction but is retrained from moving in a second direction. In one embodiment, the second direction is opposite the first direction.

In one embodiment, the anchor includes a lock member and the lock member defines a lumen. The tether extends through the lumen. In another embodiment, the anchor includes a lock member and the lock member defines a first lumen and a second lumen. The tether extends through the first lumen and the second lumen. In one embodiment, the tether includes a first portion and a second portion. The first portion is disposed between the second portion and a portion of the anchor. The second portion is configured to apply pressure on the first portion in response to a force being applied to the tether in the second direction.

In one embodiment, the anchor includes a lock member. The lock member includes a first lumen, a second lumen, a third lumen, and a fourth lumen. In some embodiments, the anchor includes a lock member. The lock member includes a first lumen, a second lumen, a third lumen, and a fourth lumen. The tether extends through the first lumen, the second lumen, the third lumen, and the fourth lumen.

In some embodiments, a first end portion of the tether is coupled to the support member and a second end portion is disposed proximal a bodily incision when the implant is disposed within the body of the patient.

In some embodiments, the anchor includes a lock member. The lock member has a first portion and a second portion movably coupled to the first portion. In some embodiments, the anchor includes a lock member. The lock member includes a first portion and a second portion pivotally coupled to the first portion.

In some embodiments, an implant includes a support member configured to be placed within a body of a patient and provide support to a portion of the body of the patient, a tether coupled to an end portion of the support member, and an anchor configured to be disposed within a tissue of the body of the patient to help retain the implant in place within the body of the patient. The anchor includes a lock member having a first portion and a second portion movably coupled to the first portion. The lock member has a first configuration and a second configuration. The tether is coupled to the lock member such that the tether may move with respect to the lock member in a first direction but is retrained from moving in a second direction when the lock member is in its first configuration. The tether being coupled to the lock member such that the tether may move with respect to the lock member in the first direction and the second direction when the lock member is in its second configuration.

In some embodiments, the second portion of the lock member is pivotally coupled to the first portion of the lock member. In some embodiments, the second portion of the lock member is pivotally coupled to the first portion of the lock member and the implant includes an activation member coupled to the first portion of the lock member.

In some embodiments, a portion of the tether is disposed between the first portion of the lock member and the second portion of the lock member. In some embodiments, a portion of the tether is disposed between the first portion of the lock member and the second portion of the lock member. The first portion of the lock member is configured to contact the portion of the tether when the lock member is in its first configuration and a force in the second direction is applied to the tether.

In some embodiments the implant includes an activation member coupled to the first portion of the lock member.

In some embodiments a method of placing an implant within a body of a patient includes making an incision in the body of the patient, inserting the implant into the body of the patient through the incision, the implant including a support member, placing the implant within the body of the patient such that the support member provides support to a portion of the body of the patient, closing the incision, and adjusting the tension of the implant after closing the incision.

In some embodiments, the adjusting includes applying a force to a tether that extends from the implant and is coupled to the support member. In some embodiments, the implant includes an anchor having a lock member and the adjusting includes applying a force to an activation member that is coupled to a portion of the lock member and applying a force to the portion of the body supported by the support member.

In some embodiments the implant includes a tether having a first end portion coupled to the support member and extends through a lumen defined by an anchor and the placing includes placing a second end portion of the tether proximal the incision.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implant, comprising:
   a support member configured to be placed within a body of a patient and provide support to a portion of the body of the patient;
   a tether coupled to an end portion of the support member, the tether including a first portion and a second portion; and
   an anchor adjustably coupled to the tether, the anchor configured to be disposed within a tissue of the body of the patient to help retain the implant in place within the body of the patient, the anchor including a lock member disposed within a cavity of the anchor, the lock member includes a first lumen, a second lumen, a third lumen, and a fourth lumen, the tether configured to extend through the first lumen in a first direction, through the second lumen in a second direction, through the third lumen in the first direction, and through the fourth lumen in the second direction, the second direction being opposite to the first direction,
   wherein the lock member includes a first portion and a second portion, the second portion configured to move with respect to the first portion of the lock member,
   wherein the first portion of the tether is disposed between the first portion of the lock member and the second portion of the lock member.

2. The implant of claim 1, wherein the first lumen, the second lumen, the third lumen, and the fourth lumen are fully enclosed lumens, the tether is configured to extend through the first fully enclosed lumen, the second fully enclosed lumen, the third fully enclosed lumen, and the fourth fully enclosed lumen.

3. The implant of claim 1, wherein a first end portion of the tether is coupled to the support member and a second end portion is configured to be disposed proximal a bodily incision when the implant is disposed within the body of the patient.

4. The implant of claim 1, wherein the first portion of the lock member is configured to be pivotally coupled to the second portion of the lock member.

5. The implant of claim 1, wherein the tether extends through the first portion of the lock member and the second portion of the lock member.

6. The implant of claim 1, wherein the first portion of the lock member is configured to apply a pressure against the first portion of the tether when an end portion of the tether is pulled in a direction away from the anchor and the lock member is in a first configuration.

7. An implant, comprising:
   a support member configured to be placed within a body of a patient and provide support to a portion of the body of the patient;
   a tether coupled to an end portion of the support member, the tether including a first portion and a second portion; and
   an anchor configured to be disposed within a tissue of the body of the patient to help retain the implant in place within the body of the patient, the anchor including a body and a plurality of barbs radially disposed around the body of the anchor, the anchor including a lock member disposed within a cavity of the body of the anchor, the lock member having a first portion and a second portion movably coupled to the first portion of the lock member, the lock member having a first configuration and a second configuration,
   the tether being coupled to the lock member such that the tether may move with respect to the lock member in a first direction and is restrained from moving in a second direction when the lock member is in its first configuration, the tether being coupled to the lock member such that the tether may move with respect to the lock member in the first direction and the second direction when the lock member is in its second configuration, and
   when the lock member is in the first configuration, the first portion of the tether is disposed between the second portion of the tether and the lock member such that the second portion of the tether is configured to apply a pressure or force against the first portion of the tether when an end portion of the tether is pulled in a direction away from the anchor.

8. The implant of claim 7, wherein the second portion of the lock member is pivotally coupled to the first portion of the lock member, the second portion of the lock member defining a plurality of lumens through which the tether extends, the first portion of the lock member defining a lumen through which the tether extends.

9. The implant of claim 8, further comprising:
   an activation member coupled to the first portion of the lock member.

10. The implant of claim 7, wherein a portion of the tether is disposed between the first portion of the lock member and the second portion of the lock member.

11. The implant of claim 7, wherein a portion of the tether is disposed between the first portion of the lock member and the second portion of the lock member, the first portion of the lock member is configured to contact the portion of the tether when the lock member is in its first configuration and a force in the second direction is applied to the tether.

12. The implant of claim 7, further comprising:
an activation member coupled to the first portion of the lock member.

13. A method of placing an implant within a body of a patient, comprising:
making an incision in the body of the patient;
inserting the implant into the body of the patient through the incision, the implant including a support member, and an anchor coupled to the support member via a suture having a first portion and a second portion, the anchor including a lock member disposed within a cavity of the anchor, the lock member including a first portion and a second portion, the second portion configured to move with respect to the first portion of the lock member, the suture extending through the first portion and the second portion of the lock member, the lock member includes a first lumen, a second lumen, a third lumen, and a fourth lumen;
extending the suture through the first lumen in a first direction, through the second lumen in a second direction, through the third lumen in the first direction, and through the fourth lumen in the second direction, the second direction being opposite to the first direction
placing the implant within the body of the patient such that the anchor is disposed within pelvic tissue and the support member provides support to a portion of the body of the patient;
disposing a portion of the suture outside the body of the patient proximate to the incision;
closing the incision; and
adjusting a tension of the implant after closing the incision by pulling on the portion of the suture outside of the body of the patient such that the second portion of the suture applies a pressure or force against the first portion of the suture.

14. The method of claim 13, wherein the adjusting includes applying a force to an activation member that is coupled to a portion of the lock member and applying a force to the portion of the body of the patient supported by the support member.

* * * * *